United States Patent [19]
Greig

[11] Patent Number: 4,969,889
[45] Date of Patent: Nov. 13, 1990

[54] INSTRUMENT FOR LOCATING A HOLE

[75] Inventor: Kevin M. Greig, Warsaw, Ind.

[73] Assignee: Zimmer, Inc., Warsaw, Ind.

[21] Appl. No.: 945,130

[22] Filed: Dec. 22, 1986

[51] Int. Cl.$^5$ .............................................. A61F 5/04
[52] U.S. Cl. ...................................... 606/97; 606/96
[58] Field of Search ............ 128/92 R, 92 V, 92 VV, 128/92 VD, 329 R; 606/86, 96, 97, 101, 104

[56] References Cited

U.S. PATENT DOCUMENTS

| | | | |
|---|---|---|---|
| 2,933,679 | 4/1960 | Bray | 324/41 |
| 3,293,544 | 12/1966 | Seng | 324/41 |
| 3,363,208 | 1/1968 | Balet | 335/285 |
| 4,418,422 | 11/1983 | Richter et al. | 128/92 VD |
| 4,485,815 | 12/1984 | Amplatz et al. | 128/329 R |
| 4,552,134 | 11/1985 | Binard | 128/1.5 |
| 4,621,628 | 11/1986 | Brudermann | 128/92 R |
| 4,625,718 | 12/1986 | Olerud et al. | 128/92 VD |
| 4,667,664 | 5/1987 | Taylor et al. | 128/92 VV |

FOREIGN PATENT DOCUMENTS 0187283  7/1986  European Pat. Off.

Primary Examiner—C. Fred Rosenbaum
Assistant Examiner—Kathleen A. Daley
Attorney, Agent, or Firm—Paul D. Schoenle

[57] ABSTRACT

An instrument for locating a hole of an intramedullary nail includes an end with a sleeve to carry a pin. The sleeve is substantially translucent when subjected to x-ray visualization and the pin is opaque so that the pin can be aligned with the hole of the intramedullary nail.

3 Claims, 1 Drawing Sheet

INSTRUMENT FOR LOCATING A HOLE

The present invention relates to an instrument for locating a hole within an internal member when the latter is disposed within a body.

In U.S. Pat. No. 4,552,134 equipment is shown for the purpose of locating a cross pin hole in a metal body which has been disposed within a bone. As noted therein, a distal pin must intersect a hole of an intramedullary nail to fixedly retain the latter in engagement with a portion of a fractured bone. However, the intramedullary nail follows a random direction during insertion so that finding the location of the distal hole in the intramedullary nail is difficult in the absence of x-ray equipment. However, the visual representation obtained by the x-ray equipment is not clearly focused so that the positioning of a cross pin is less than accurate in view of the wide variation possible from the x-ray visual representation. Moreover, the repeated use of x-ray equipment during surgery is not favorably accepted by the operating room staff so that a reduction of usage is desirable.

The present invention provides a clear target utilizing x-ray visual representations for positioning a pin in substantial accurate alignment with a distal hole of an intramedullary nail or internal member. To this end, an instrument is constructed from a metal such as aluminum with one end adapted for manual disposition by operating room staff. The other end of the instrument is provided with a cylindrical aperture to receive a sleeve made from any material which is x-ray translucent to allow x-rays to pass through so that it is not detected on x-ray. The sleeve defines an opening for receiving a Steinman Pin which extends outwardly from the cylindrical aperture to engage a portion of a fractured bone that has an intramedullary nail disposed inside. With the aperture defining a circular surface and the sleeve disposing the Steinman Pin in the center of the circular aperture, an x-ray taken from the top of the other end will visually represent the aperture as a circle with the Steinman Pin as a target point in the center. Moreover, the intramedullary nail will appear within the circle with a hole visually represented. As the handle is moved, the circle and target point will also move to permit centering of the target point within the hole. At that point, the Steinman Pin is aligned with the distal hole of the intramedullary nail so that insertion of the Steinman Pin into the bone will accurately dispose the Steinman Pin through the distal hole. Thereafter, the Steinman Pin acts as a key to guide the direction of a drill or screw to secure the intramedullary nail to the bone. In order to enhance the visual representation obtained by x-ray, the smallest dimension of the cylindrical aperture is larger than a width dimension of the intramedullary nail.

It is an object of the present invention to provide an instrument which accurately represents the position of an intramedullary nail within a bone.

It is a further object of the invention to utilize x-ray equipment in an efficient manner to locate a distal hole in an intramedullary nail.

Turning to the accompanying drawings.

Figure 1:
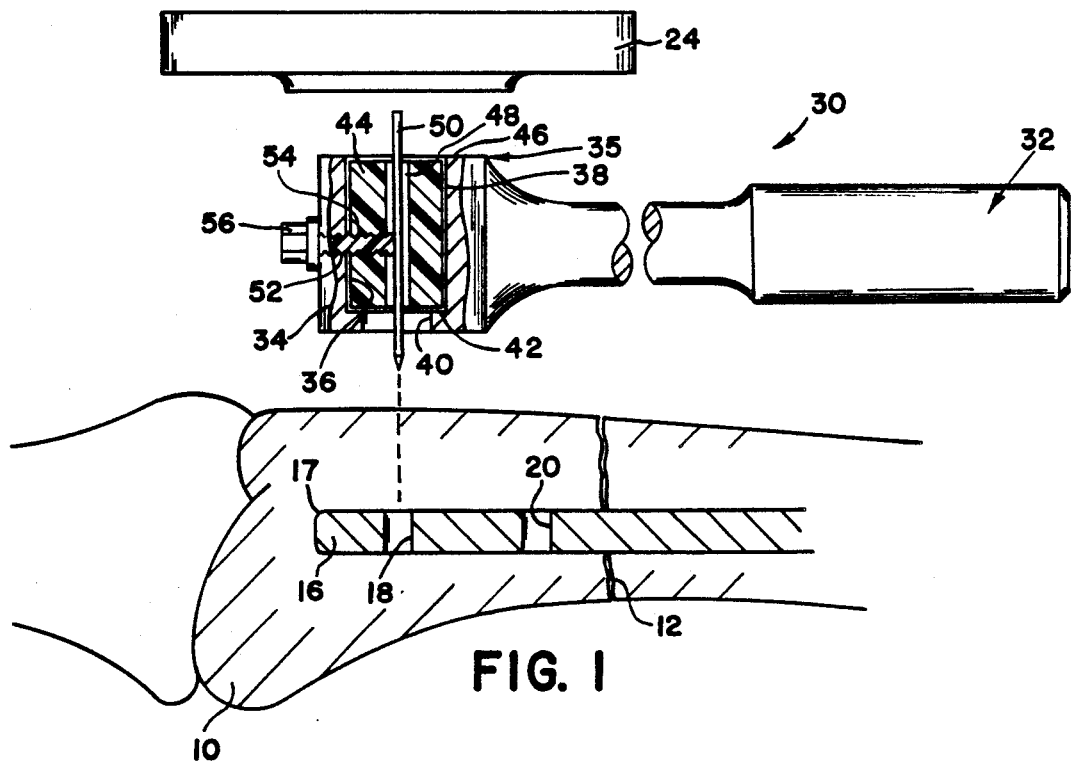
FIG. 1 illustrates a fractured bone with an intramedullary nail disposed therein and an instrument of the present invention adapted for locating a distal hole of the intramedullary nail.
Figure 2:
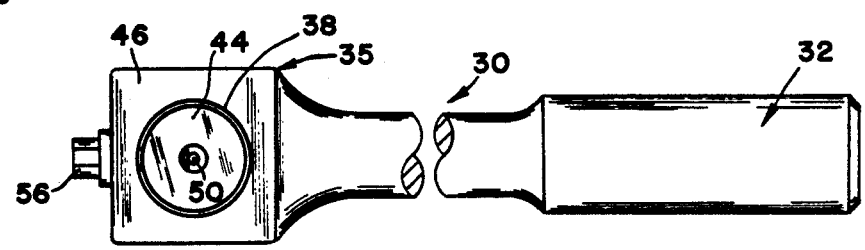
FIG. 2 shows a top view of the instrument.

A fractured bone 10 with a fracture site 12 has been exposed via an incision of the tissue surrounding the fractured bone 10. An intramedullary nail 16 with distal holes 18 and 20 is disposed within the bone 10 to extend across the fracture site 12. When the intramedullary nail 10 is secured to the bone 10, it will provide load bearing support to enable the patient to move about while the bone at the fracture site is healing. With the bone surrounding the intramedullary nail 16 it is not possible to visually locate the holes 18 and 20 so that the positioning of screws or pins within the holes 18 and 20 must be accommodated by an x-ray machine shown schematically at 24 to visually represents opaque structures.

An instrument 30 constructed in accordance with the present invention is disposed between the x-ray machine 24 and the fractured bone 10. The instrument 30 comprises a handle 32 at one end remote from the x-ray machine so that radiant energy is not focused at the one end. The other end 34 forms a cube 35 with a cylindrical stepped aperture 36 extending through the cube. The aperture 36 defines a large diameter section 38 and a small diameter section 40 with a shoulder 42 therebetween. A sleeve 44 is disposed within the aperture 36 to abut the shoulder 42 when substantially flush with a top surface 46 of the end 34. The sleeve 44 forms an opening 48 to receive a Steinman Pin 50 and threaded bores 52 and 54 in the end 34 and sleeve 44, respectively, receive a set screw 56 to secure the sleeve 44 and pin 50 within the end 34.

The handle 32 and cube 35 are constructed of aluminum which is more opaque than bone when visually represented on an x-ray machine. The sleeve 44 and set screw 56 are constructed of a plastic-like material such as Delrin which is more translucent than bone when visually represented in an x-ray machine.

Figure 3:
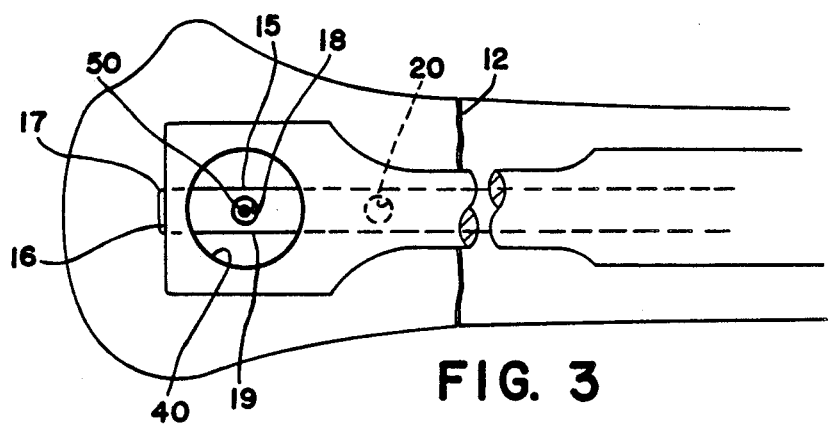
FIG. 3 shows a top view of the instrument, fractured bone and intramedullary nail as visually represented by an x-ray picture.

During surgery the fractured bone is stabilized via manipulation to provide for alignment despite the fracture 12. The intramedullary nail 16 is driven into the bone to extend across the fracture site and maintain alignment between the portions of bone on both sides of the fracture. In order to secure the distal end 17 of the intramedullary nail 16 a pair of screws (not shown) will be drilled into the bone to extend through holes 18 and 20. The bone is exposed at the approximate location of the distal end 17 and the instrument 30 is positioned with the point 51 of pin 50 engaging the outer surface of bone 10. The x-ray machine 24 is positioned over the end 34 of instrument 30 to generate the visual representation shown in FIG. 3. With the sleeve 44 and the set screw 56 being translucent, the cube 35 visually forms a square in FIG. 3 with the small diameter section 40 defining a target focusing on the nail distal end 17 and hole 18. Edges 15 and 19 of the distal end 17 appear within the target 40 as well as hole 18. By moving the handle 32, the target 40 and pin 50 are moved to centrally dispose the pin 50 within the hole 18. At that time, the pin 50 is fully inserted through the hole 18 for accurate location of the pin 50 relative the hole 18. The hole created by the pin 50 provides a guide for a drill to enlarge the hole allowing fixation of the distal end 17 to the bone 10 via a screw or pin driven coaxially with the pin 50 through the bone 10 and the hole 18.

Similarly, the hole 20 can be located for additional fixation of the bone to the distal end 17 of the intramedullary nail.

I claim:

1. An instrument for locating a hole of an internal member within a body when the internal member and body are subjected to radiant energy, the body being partially translucent and the internal member being substantially opaque such that the radiant energy cooperates with an x-ray machine or the like to generate a visual representation of the internal member, the instrument including a handle at one end adapted for manual disposition of the instrument relative the body and x-ray machine and an opposite end of the handle being substantially opaque and forming an aperture to receive a translucent sleeve, the translucent sleeve forming an opening to receive an opaque pin, and means for retaining the translucent sleeve within the opposite end and for retaining the opaque pin within the translucent sleeve, and the opposite end being readily movable between the body and the x-ray machine by manual disposition of the one end whereby the instrument one end substantially forms a single extension protruding from the area subjected to radiant energy to accommodate spacing between the x-ray machine and the body.

2. The instrument of claim 1 in which the opposite end aperture forms a stepped bore with a shoulder extending transversely between a large diameter bore and a small diameter bore, the translucent sleeve abuts the transversely extending shoulder and the small diameter bore defines a target on the x-ray machine or the like for viewing the internal member when radiant energy is directed into the opposite end of the instrument, the translucent sleeve, and the internal member.

3. The instrument of claim 1 in which the opposite end aperture defines a dimension which is greater than a width dimension for the internal member so that the complete width of the internal member is visible in response to operation of the x-ray machine or the like.

* * * * *